United States Patent
Zucker

(10) Patent No.: US 12,207,882 B2
(45) Date of Patent: Jan. 28, 2025

(54) METHODS AND SYSTEMS FOR PLANNING A SURGICAL PROCEDURE

(71) Applicant: Mazor Robotics Ltd., Caesarea (IL)

(72) Inventor: Ido Zucker, Tel Aviv (IL)

(73) Assignee: Mazor Robotics Ltd., Caesarea (IL)

( * ) Notice: Subject to any disclaimer, the term of this patent is extended or adjusted under 35 U.S.C. 154(b) by 247 days.

(21) Appl. No.: 17/165,575

(22) Filed: Feb. 2, 2021

(65) Prior Publication Data

US 2022/0241015 A1    Aug. 4, 2022

(51) Int. Cl.
| | |
|---|---|
| *A61B 34/10* | (2016.01) |
| *A61B 5/00* | (2006.01) |
| *A61B 5/11* | (2006.01) |
| *G06T 5/50* | (2006.01) |
| *G06T 7/00* | (2017.01) |

(Continued)

(52) U.S. Cl.
CPC ............ *A61B 34/10* (2016.02); *A61B 5/1121* (2013.01); *A61B 5/4504* (2013.01); *A61B 5/4566* (2013.01); *A61B 5/4827* (2013.01); *A61B 5/4887* (2013.01); *G06T 5/50* (2013.01); *G06T 7/0012* (2013.01); *G06T 7/11* (2017.01); *G06T 7/70* (2017.01); *G06T 19/00* (2013.01); *G06V 10/758* (2022.01); *G16H 20/40* (2018.01); *G16H 30/20* (2018.01); *G16H 30/40* (2018.01); *G16H 50/20* (2018.01); *G16H 50/50* (2018.01); *A61B 2034/105* (2016.02); *G06T 2207/10081* (2013.01); *G06T 2207/10088* (2013.01); *G06T 2207/20221* (2013.01); *G06T 2207/30012* (2013.01); *G06T 2219/004* (2013.01); *G06V 2201/03* (2022.01)

(58) Field of Classification Search
CPC .................. G06T 7/11; G06T 7/0012; G06T 2207/30008; G06T 2207/30012; G06T 7/60; G06T 2210/41; G06T 2207/30004; G06T 7/70; G06T 5/50; G06T 19/00; G06T 2207/10081; G06T 2207/10088; G06T 2207/20221; G06T 2219/004; A61B 34/10; A61B 5/45; A61B 2034/108; A61B 2034/105; A61B 6/505; A61B 2034/102; A61B 5/4504; A61B 8/0875; A61B 5/103; A61B 5/1121; A61B 5/4566; A61B 5/4827; A61B 5/4887; G16H 20/40; G16H 50/50; G16H 50/20; G16H 50/30; G16H 30/40; G16H 30/20; G06V 2201/03; G06V 10/25; G06V 10/761; G06V 10/758

See application file for complete search history.

(56) References Cited

U.S. PATENT DOCUMENTS

| | | | |
|---|---|---|---|
| 8,457,930 B2 * | 6/2013 | Schroeder | G06F 30/20 703/1 |
| 10,166,019 B2 * | 1/2019 | Nawana | A61B 34/25 |

(Continued)

*Primary Examiner* — Aaron W Carter
*Assistant Examiner* — Courtney Joan Nelson
(74) *Attorney, Agent, or Firm* — Sheridan Ross P.C.

(57) ABSTRACT

Systems and methods for planning a surgical procedure are provided. Information corresponding to an examination of a patient and an image of the patient may be received. The information and the image may be inputted into an analytical model configured to identify a pathology location. A needed surgical modification of the patient anatomy may be automatically identified. At least a portion of an anatomical element in a three-dimensional model of the patient anatomy may be automatically labeled.

20 Claims, 4 Drawing Sheets

(51) Int. Cl.
  *G06T 7/11*   (2017.01)
  *G06T 7/70*   (2017.01)
  *G06T 19/00*  (2011.01)
  *G06V 10/75*  (2022.01)
  *G16H 20/40*  (2018.01)
  *G16H 30/20*  (2018.01)
  *G16H 30/40*  (2018.01)
  *G16H 50/20*  (2018.01)
  *G16H 50/50*  (2018.01)

(56) References Cited

U.S. PATENT DOCUMENTS

| | | | | |
|---|---|---|---|---|
| 10,292,770 | B2* | 5/2019 | Ryan | A61B 17/7002 |
| 10,517,681 | B2* | 12/2019 | Roh | A61B 34/20 |
| 10,902,944 | B1* | 1/2021 | Casey | A61B 34/25 |
| 2010/0261993 | A1* | 10/2010 | van der Kouwe | G01R 33/482 |
| | | | | 600/410 |
| 2012/0143090 | A1* | 6/2012 | Hay | A61B 6/505 |
| | | | | 600/587 |
| 2015/0088185 | A1* | 3/2015 | Naraghi | A61B 17/0218 |
| | | | | 606/192 |
| 2019/0029757 | A1* | 1/2019 | Roh | A61B 34/20 |
| 2019/0139641 | A1 | 5/2019 | Itu et al. | |
| 2019/0188848 | A1* | 6/2019 | Madani | G16H 30/40 |
| 2019/0274575 | A1* | 9/2019 | Kim | A61B 5/055 |
| 2020/0273578 | A1 | 8/2020 | Kutzko et al. | |
| 2020/0303071 | A1 | 9/2020 | Miller et al. | |
| 2020/0373013 | A1* | 11/2020 | Cao | G06T 7/0014 |
| 2021/0313062 | A1* | 10/2021 | Junio | G06T 7/0012 |

* cited by examiner

METHODS AND SYSTEMS FOR PLANNING A SURGICAL PROCEDURE

FIELD

The present technology generally relates to planning surgical procedures, and relates more particularly to automatically identifying surgical modifications.

BACKGROUND

Planning one or more surgical steps for a surgical plan is based on several factors and inputs. Surgeons may identify one or more surgical procedures to perform to alleviate patient pain and/or discomfort. Surgical robots may assist a surgeon or other medical provider in carrying out the one or more surgical procedures, or may complete the one or more surgical procedures autonomously.

SUMMARY

Example aspects of the present disclosure include:

A method for planning a surgical procedure according to at least one embodiment of the present disclosure comprises receiving, at a processor, information corresponding to an examination of a patient, the examination conducted by a human; receiving, at the processor, an image of a patient anatomy; inputting, using the processor, the information and the image into an analytical model configured to identify, using artificial intelligence, a pathology location; automatically identifying, with the processor and based on the pathology location, a needed surgical modification of the patient anatomy; and automatically labeling, with the processor and based on the needed surgical modification, at least a portion of an anatomical element in a three-dimensional model of the patient anatomy.

Any of the aspects herein, further comprising: automatically generating, with the processor, instructions for at least one surgical step to remove the portion of the anatomical element.

Any of the aspects herein, wherein the surgical modification corresponds to a decompression procedure.

Any of the aspects herein, wherein the patient examination identifies an initial spinal level at which to perform the decompression procedure.

Any of the aspects herein, further comprising: receiving, at the processor, at least one medical record corresponding to the patient; wherein the inputting further comprises inputting the at least one medical record into the analytical model.

Any of the aspects herein, wherein the image is obtained from a CT scan or an MM scan.

Any of the aspects herein, wherein the image is a first image and the method further comprises: receiving, by the processor, a second image; and automatically combining, by the processor, the first image and the second image.

Any of the aspects herein, wherein the first image comprises detailed soft tissue information and the second image comprises detailed bony tissue information.

Any of the aspects herein, wherein the information includes results of one or more of a soft tissue tenderness test, a range of motion test, or a straight leg raise test.

Any of the aspects herein, wherein the patient anatomy corresponds to a spine of the patient, the method further comprising: segmenting the image to identify individual vertebra of the spine.

A method for planning a decompression procedure according to at least one embodiment of the present disclosure comprises receiving, at a processor, information corresponding to a patient examination; receiving, at the processor, an image of a spinal region of a patient; and identifying, with the processor and using artificial intelligence, a location of spinal stenosis based on the information and the image.

Any of the aspects herein, further comprising: automatically labeling, with the processor and in a model of the spinal region of the patient, a portion of at least one vertebra to remove during a decompression procedure targeting the spinal stenosis.

Any of the aspects herein, further comprising: determining a spinal level at which to perform the decompression procedure based on the identified location of spinal stenosis.

Any of the aspects herein, wherein the identifying is further based on at least one electronic medical record received at the processor.

Any of the aspects herein, further comprising determining whether the spinal stenosis is a lateral stenosis or a central stenosis.

Any of the aspects herein, further comprising: automatically grading, by the processor, the identified spinal stenosis.

Any of the aspects herein, further comprising: segmenting, with the processor, the spinal region as depicted in the image to define boundaries of individual elements of the spinal region; and identifying, with the processor, one or more spinal nerves in the image.

Any of the aspects herein, further comprising: automatically generating, by the processor, instructions for at least one surgical step to remove the identified portion of the at least one vertebra.

A system for performing a decompression procedure according to at least one embodiment of the present disclosure comprises an interface; at least one processor; and a memory storing instructions for execution by the at least one processor that, when executed, cause the at least one processor to: receive, via the interface, information corresponding to a patient examination, receive a three-dimensional image of at least a portion of an anatomy of a patient, identify, using artificial intelligence, a predicted location of an anatomical abnormality, automatically label, in the three-dimensional image and based on the predicted location, a portion of at least one anatomical element to surgically modify.

Any of the aspects herein, wherein the memory stores additional instructions for execution by the at least one processor that, when executed, further cause the at least one processor to: compare an anatomical feature at the location of the anatomical abnormality with a corresponding feature at a different location.

Any of the aspects herein, wherein the three-dimensional image is obtained from a CT scan or an MRI scan.

Any of the aspects herein, wherein the information corresponds to a patient description, provided during the patient examination, of at least one symptom experienced by the patient.

Any of the aspects herein, wherein the anatomical abnormality is a spinal stenosis.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
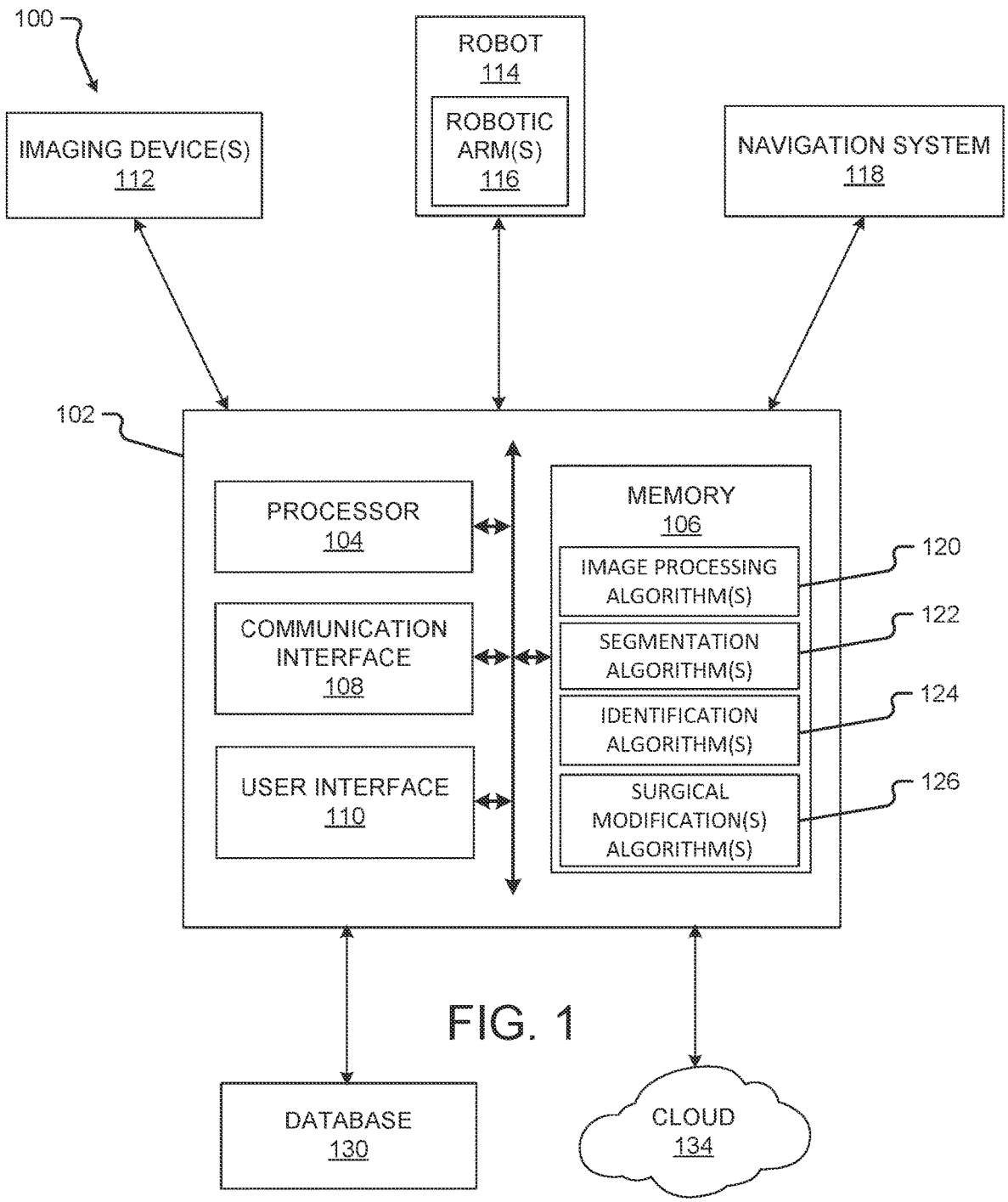
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

While planning for a spinal surgical procedure, doctors often use imaging to determine a position of a pathology that may be causing pressure on a spinal nerve or a spinal cord of a patient. However, the imaging may not be sufficient to locate the pathology (which may be, for example, an obstruction). By combining clinical evaluation with the image processing, accuracy of the diagnosis of the pathology may be increased or improved. A doctor may use a description of the pain from the patient along with the results of the clinical examination (which may include a soft tissue tenderness test, a range of motion test, a straight leg raise test (to determine if a nerve root irritation exists), etc.) to locate the pathology.

Embodiments of the present disclosure provide for standardizing and automating a medical diagnostic process, using a combination of clinical examination results, image processing and artificial intelligence to aid with the diagnosis. The doctor's examination may be incorporated into an artificial intelligence (AI) model along with one or more images of the relevant patient anatomy and one or more patient medical records. The combination of these inputs enables improved accuracy of the AI model.

Embodiments of the present disclosure provide technical solutions to one or more of the problems of (1) automatically identifying an anatomical abnormality, (2) automatically planning a surgical procedure, (3) automatically labelling an anatomical abnormality in a three-dimensional model or a two-dimensional image, (4) improving the accuracy of diagnoses; (5) improving a consistency of diagnoses; and/or (6) improving patient safety.

Turning first to FIG. 1, a block diagram of a system 100 according to at least one embodiment of the present disclosure is shown. The system 100 may be used to plan a surgical procedure and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200, 300, and/or 400 described herein, or of any other methods. The memory 106 may store, for example, one or more image processing algorithms 120, one or more segmentation algorithms 122, one or more identification algorithms 124, and/or one or more surgical modification algorithms 126. Such instructions or algorithms may, in some embodiments, be organized into one or more applications, modules, packages, layers, or engines. The algorithms and/or instructions may cause the processor 104 to manipulate data stored in the memory 106 and/or received from or via the user interface 110, the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, a thermographic camera (e.g., an infrared camera), an optical camera, a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic field generators and/or electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The system 100 or similar systems may be used, for example, to carry out one or more aspects of any of the methods 200, 300, and/or 400 described herein. The system 100 or similar systems may also be used for other purposes.

Figure 2:
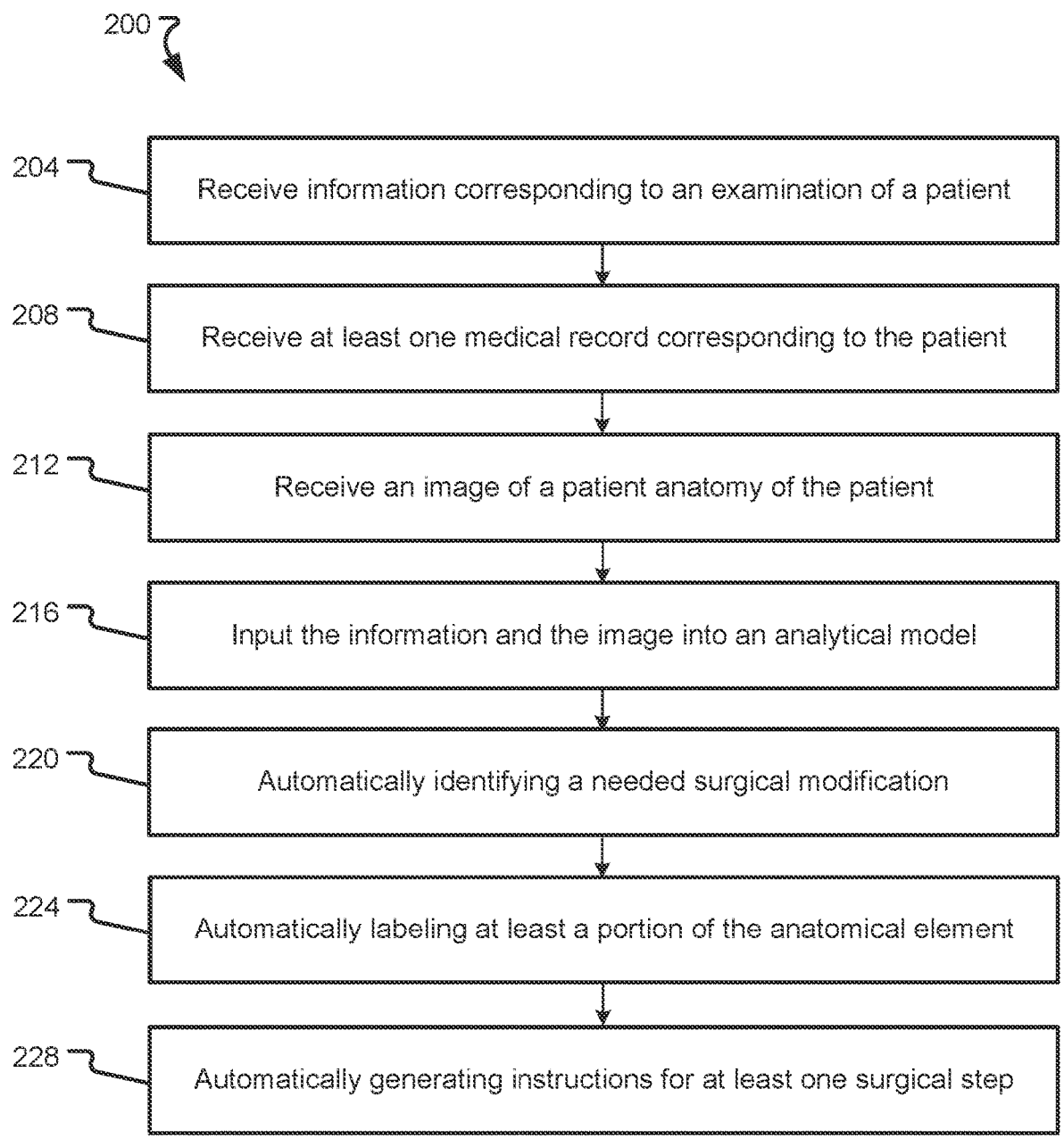
FIG. 2 is a flowchart according to at least one embodiment of the present disclosure.

FIG. 2 depicts a method 200 that may be used, for example, for planning a surgical procedure.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing instructions stored in a memory such as the memory 106. The instructions may correspond to one or more steps of the method 200 described below. The instructions may cause the processor to execute one or more algorithms, such as an image processing algorithm 120, a segmentation algorithm 122, one or more identification algorithms 124, and/or one or more surgical modification algorithms 126.

The method 200 comprises receiving, by the processor, information corresponding to an examination of a patient (step 204). The information may be received via a user interface such as the user interface 110 and/or a communication interface such as the communication interface 108 of a computing device such as the computing device 102, and may be stored in a memory such as the memory 106 of the computing device. The information may also be received from an external database or image repository (e.g., a hospital image storage system, such as a picture archiving and communication system (PACS), a health information system (HIS), and/or another system for collecting, storing, managing, and/or transmitting electronic medical records including image data), and/or via the Internet or another network.

The examination may be conducted by a human such as a surgeon or other medical provider. The resulting information may include results of a soft tissue tenderness test, a range of motion test, and/or a straight leg raise test. The information may also include a patient description of at least one symptom experienced by the patient. In some embodiments, the information may include identification of an initial spinal level at which to perform a surgical procedure (such as a decompression procedure) and/or an initial diagnosis (e.g., a type of spinal stenosis). It will be appreciated that the information can include any input from a surgeon, medical provider, and/or the patient corresponding to the patient.

The method 200 also comprises receiving, by the processor, at least one medical record corresponding to the patient (step 208). The medical record may be received via a user interface such as the user interface 110 and/or a communication interface such as the communication interface 108 of a computing device such as the computing device 102, and may be stored in a memory such as the memory 106 of the computing device. The medical record may also be received from an external database or image repository (e.g., a hospital image storage system, such as a picture archiving and communication system (PACS), a health information system (HIS), and/or another system for collecting, storing, managing, and/or transmitting electronic medical records including image data), and/or via the Internet or another network. The at least one medical record may include a patient's age, weight, height, pre-existing conditions, current medication, medical history, and/or any historical and/or current information about the patient.

The method 200 also comprises receiving, by the processor, an image of a patient anatomy of the patient (step 212). The image may be received via a user interface such as the user interface 110 and/or a communication interface such as the communication interface 108 of a computing device such as the computing device 102, and may be stored in a memory such as the memory 106 of the computing device. The image may also be received from an external database or image repository (e.g., a hospital image storage system, such as a picture archiving and communication system (PACS), a health information system (HIS), and/or another system for collecting, storing, managing, and/or transmitting electronic medical records including image data), and/or via the Internet or another network. In other embodiments, the image may be received or obtained from an imaging device such as the imaging device 112, which may be any imaging device such as an MRI scanner, a CT scanner, any other X-ray based imaging device, or an ultrasound imaging device. The image may also be generated by and/or uploaded to any other component of a system such as the system 100. In some embodiments, the image may be indirectly received via any other component of the system or a node of a network to which the system is connected.

The image may comprise one or more 2D images, one or more 3D images, a 3D model, or a combination of one or more 2D images and one or more 3D images. In some embodiments, one imaging device may be used to obtain the image. In other embodiments, multiple imaging devices may be used to obtain the image. In examples wherein more than one image is received or multiple images are used to construct a 3D image, a first imaging device may obtain a first one of the images independently of a second imaging device obtaining a second one of the images. In another example, at least a first one of the images may be obtained with a first imaging device and at least a second one of the images may be obtained with a second imaging device.

The image may be processed using an image processing algorithm such as the image processing algorithm 120 to identify one or more features in the image, as will be described below. In some embodiments, feature recognition (using, e.g., an edge detection or other feature recognition algorithm) may be used to identify a feature of an anatomical element, a tool, and/or an instrument. For example, a contour of a vertebra, femur, or other bone may be identified in the image. In other embodiments, segmentation (using, e.g., a segmentation algorithm such as the segmentation algorithm 122) may be used to identify an anatomical element in the image.

The image may depict patient anatomy such as a spinal region. In some embodiments, the image may be a first image and the step 212 may also include receiving, by the processor, a second image. The first image may comprise detailed soft tissue information (e.g., the first image may be obtained from an MRI scan) and the second image may comprise detailed bony tissue information (e.g., the second image may be obtained from a CT scan). The step 212 may also include automatically combining, by the processor, the first image and the second image (and/or image data corresponding to the first image and image data corresponding to the second image). In some embodiments, combining the first image and the second image includes combining detailed soft tissue information and detailed bony tissue information.

The method 200 also comprises inputting, using the processor, the information and the image into an analytical model (step 216). The analytical model is configured to identify a pathology location using artificial intelligence. In some embodiments, the step 216 also comprises inputting the at least one medical record obtained in step 208, and/or data corresponding to the at least one medical record, into the analytical model to facilitate identification of the pathology location. In some embodiments, the analytical model may use an identification algorithm such as the identification algorithm 124 to identify the pathology location. Training data may be used to train the identification algorithm to identify the pathology location. The training data may include historical data (including, e.g., historical patient examination information, historical patient medical records, historical patient images, and/or any other data from past patients with the same or similar metrics as the patient and/or the same or similar pathologies as the patient, etc.).

In some instances, more than one possible pathology location may be identified (using, for example, the identification algorithm) in the image(s). In such instances, the information provided from the patient examination (which in some embodiments, may not be image-based) may be used to identify one or more of the possible pathology locations that is causing pain and/or discomfort to a patient. In other words, the information provided from the patient examination may be used to pinpoint the pathology location (s) that may be attributing to pain and/or discomfort of a patient. Thus, unnecessary surgical procedures to correct pathologies that are not affecting the patient may be avoided.

The pathology location may include information about a pose, a position, or an orientation of the pathology. For example, in some embodiments, the pathology may be an obstruction and the pathology location may specify a pose, a position, or an orientation of the obstruction.

The method 200 also comprises automatically identifying, with the processor, a needed surgical modification of the patient anatomy (step 220). The identifying may be based on the pathology location. In some embodiments, the identifying may use a surgical modification algorithm such as the surgical modification algorithm 126 to identify the needed surgical modification. Training data may be used to train the surgical modification algorithm to identify the needed surgical modification. In some embodiments, the training data may include historical data (e.g., information about historical surgical modifications used to correct pathologies that are the same as or similar to, and/or that are in the same or a similar location as, the pathology of the patient in question). In other embodiments, the training data may also include a surgeon or medical provider input. For example, the training data may include a surgeon or medical provider identification of a surgical modification appropriate for the identified pathology.

In some embodiments, the surgical modification may correspond to a decompression procedure. For example, the pathology may be a spinal stenosis and the surgical modification to alleviate the spinal stenosis may be a decompression procedure.

The method 200 also comprises automatically labelling, with the processor, at least a portion of the anatomical element (step 224). The labelling may be based on the needed surgical modification. In some examples, the labelling may label the portion of the anatomical element in a 3D model (which may be obtained in step 212) of the patient anatomy. In other examples, the labelling may label the portion of the anatomical model in one or more 2D images (which may be obtained in step 212). For example, the needed surgical modification may indicate that a portion of a vertebra is to be removed. The labelling may then label the portion of the vertebra to remove in the 3D model and/or in the one or more 2D images.

The method 200 also comprises automatically generating instructions for at least one surgical step (step 228). The at least one surgical step may be the surgical modification identified in step 220. In some embodiments, the surgical modification includes removing the portion of the anatomical element labelled in step 224. For examples, the surgical modification may include removing a portion of a vertebra. The instructions may be generated in machine readable form or human readable form. The instructions may be transmitted to a robot such as the robot 114 to cause the robot to execute the surgical step. In other embodiments, the instructions may be communicated to a surgeon or other medical provider via a user interface such as the user interface 110.

The present disclosure encompasses embodiments of the method 200 that comprise more or fewer steps than those described above, and/or one or more steps that are different than the steps described above.

Figure 3:
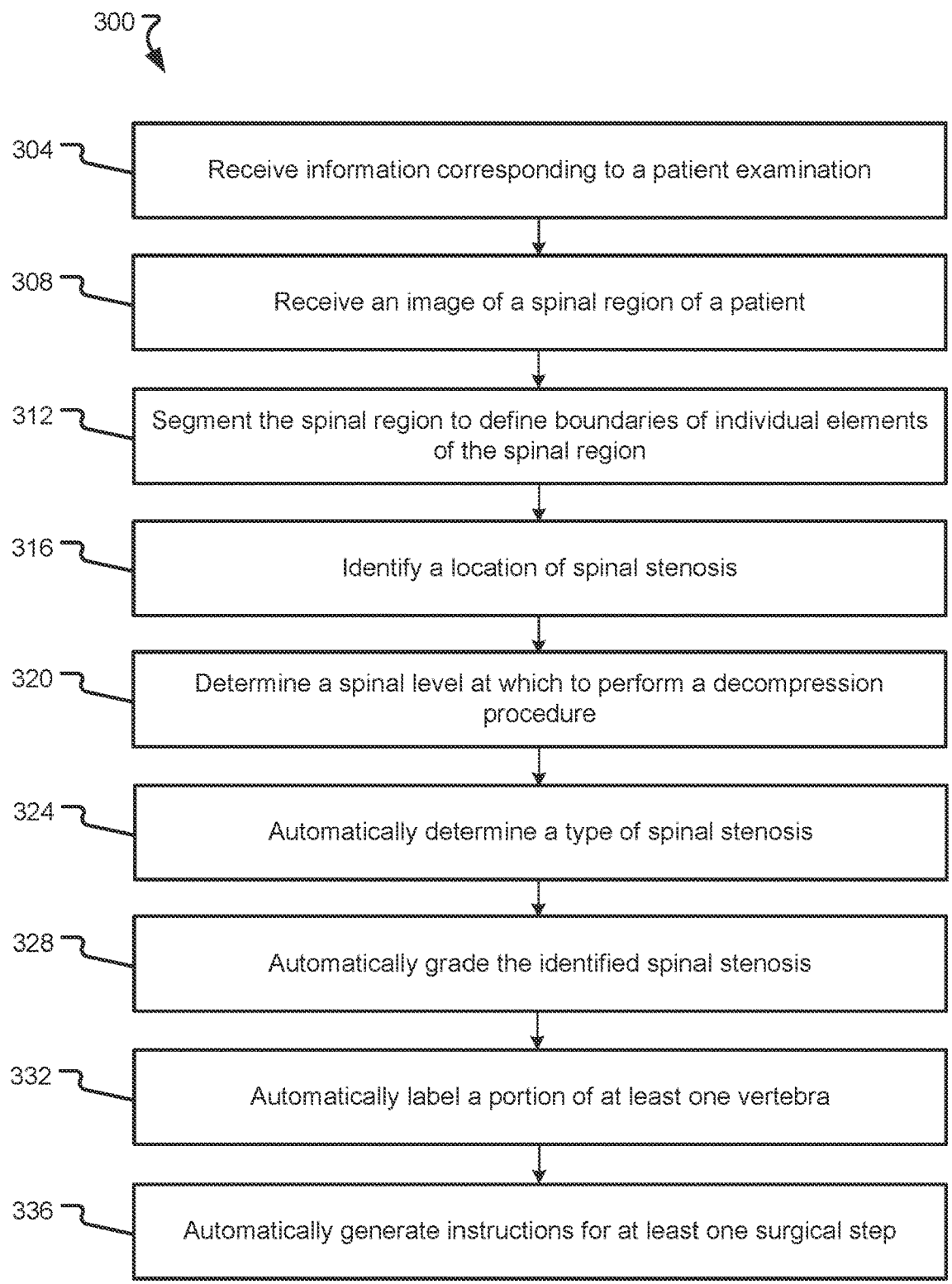
FIG. 3 is a flowchart according to at least one embodiment of the present disclosure.

FIG. 3 depicts a method 300 that may be used, for example, for planning a surgical procedure.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as an image processing algorithm 120, a segmentation algorithm 122, one or more identification algorithms 124, and/or one or more surgical modification algorithms 126.

The method 300 comprises receiving, by the processor, information corresponding to a patient examination (step 304). The step 304 may be the same as or similar to the step 204 of the method 200 described above.

The method 300 also comprises receiving, by the processor, an image of a spinal region of a patient (step 308). In some embodiments, the step 308 may be the same as or similar to step 212 of the method 200 described above. Further, the image may depict one or more vertebrae, one or more spinal nerves, and/or a spinal cord. Also in some embodiments, the step 308 may comprise receiving, by the processor, an image of an anatomical element not part of the spinal region (e.g., from a different region than the spinal region). The image may comprise one or more 3D image or 3D models, and/or one or more 2D images.

The method 300 also comprises segmenting, with the processor, the spinal region to define boundaries of individual elements of the spinal region (step 312). The segmenting may use a segmentation algorithm such as the segmentation algorithm 122 to define the boundaries of individual elements of the spinal region, such as one or more spinal nerves, vertebrae, a spinal cord, and/or the like. Training data may be used to train the segmentation algorithm to identify the boundaries of the individual elements. The training data may include historical images in which the boundaries of individual elements similar to or the same as the individual elements of the current image are defined. For example, the training data may include a plurality of vertebrae in which the boundaries of each vertebra are defined.

The method 300 also comprises identifying, with the processor, a location of spinal stenosis (step 316). The identifying may be based on the information received in step 304 and the image received in step 308. The identifying may be further based on at least one medical record received by the processor. In some embodiments, the step 316 may be the same as or similar to step 216 of the method 200 described above with respect to identifying a pathology location. More specifically and in at least one instance according to the present disclosure, a plurality of spinal stenoses may be identified in the image received in step 308. However, not all spinal stenoses may cause pain to the patient. Thus, the information received from the patient examination may be used to identify one or more spinal stenoses of the plurality of stenoses that may specifically cause the patient's pain.

In some embodiments, the identifying may be based on an analysis of how spinal nerves are spread out. When the spinal nerves are all on one side, then this may indicate that the nerves are pressured and experiencing spinal stenosis. When the spinal nerves are evenly spaced, then this may indicate that the nerves are not pressured and are likely not experiencing spinal stenosis.

The method 300 also comprises determining, with the processor, a spinal level at which to perform a decompression procedure (step 320). The determining may be based on the location of the spinal stenosis identified in step 316. In some embodiments, the information corresponding to the patient examination may include an initial determination of a spinal level at which to perform the decompression procedure. The step 320 may then be used to confirm the initial spinal level determination or to change the spinal level determination. Determining the spinal level may be useful, for example, for generating the instructions in step 336 described below.

The method 300 also comprises automatically determining, with the processor, a type of spinal stenosis (step 324). The type may be, for example, a lateral stenosis or a central stenosis. The type may be determined by identifying a portion of the vertebra causing the spinal stenosis. Determining the type of spinal stenosis may be useful, for example, for labelling a portion of at least one vertebra to remove in step 332, described below. In other words, the type of spinal stenosis may help determine, for example, which portion of the at least one vertebra to remove. Determining the type of spinal stenosis may also be useful, for example, for generating the instructions in step 336 below.

The method 300 also comprises automatically grading, with the processor, the identified spinal stenosis (step 328). The grading may include analyzing a cross-section of a spinal nerve to identify a percentage of the cross-section that is constricted. In some embodiments, the grading may grade the spinal stenosis on a grade of 0 to 3, with 3 being severe. In other embodiments, the grading may grade the spinal stenosis (as depicted in one or more images, for example) on a different numerical scale (e.g., on a scale of 1-10, with 10 being severe), or on any other scale (such as color, intensity, etc.). In some embodiments, grading the spinal stenosis may be useful for labelling a portion of at least one vertebra to remove in step 332, described below. The grading may, for example, determine how much of the at least one vertebra to remove. In other embodiments, grading the spinal stenosis may also be useful, for example, for generating the instructions in step 336 below.

The method 300 also comprises automatically labeling, with the processor, a portion of at least one vertebra to remove during a decompression procedure targeting the identified spinal stenosis (step 332). The step 328 may be the same as or similar to the step 224 of the method 200 described above. Further, the portion of the at least one vertebra, in some examples, may be labeled in a 3D image or 3D model of the spinal region (which may be obtained in step 308) of the patient. In other examples, the portion of the at least one vertebra may be labeled in one or more 2D images (which may be obtained in step 308) of the spinal region of the patient. In still other embodiments, the portion of the at least one vertebra may be labeled in both a 3D image or model and in one or more 2D images.

The method 300 also comprises automatically generating, with the processor, instructions for at least one surgical step (step 336). The step 328 may be the same as or similar to the step 228 of the method 200 described above. The instructions may also include information about the spinal level identified or confirmed in step 320, the type of spinal stenosis identified in step 324, and/or the grade of the identified spinal stenosis obtained in step 328. Such information may be, for example, communicated to a surgeon or other medical provider via a user interface such as the user interface 110.

The present disclosure encompasses embodiments of the method 300 that comprise more or fewer steps than those described above, and/or one or more steps that are different than the steps described above.

Figure 4:
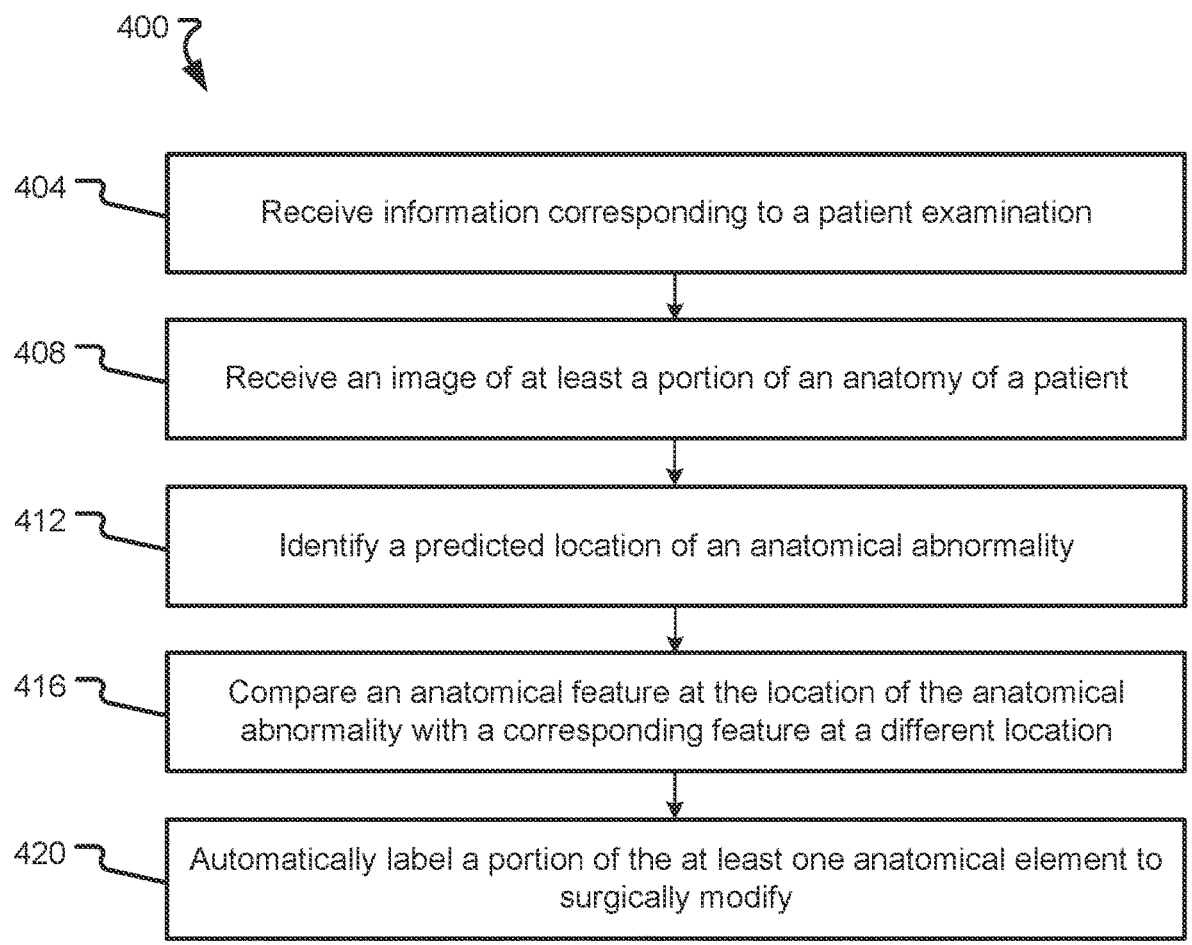
FIG. 4 is a flowchart according to at least one embodiment of the present disclosure.

FIG. 4 depicts a method 400 that may be used, for example, for planning a surgical procedure.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as an image processing algorithm 120, a segmentation algorithm 122, one or more identification algorithms 124, and/or one or more surgical modification algorithms 126.

The method 400 comprises receiving, via a user interface, information corresponding to a patient examination (step 404). In some embodiments, the step 404 may be the same as or similar to the step 204 of the method 200 described above. The user interface may be the same as or similar to the user interface 110. In some embodiments, the step 404 may also comprise receiving at least one medical record via the user interface, which medical record may be the same as or similar to (and/or may contain the same or similar information as) any other medical record described herein.

The method 400 also comprises receiving an image of at least a portion of an anatomy of a patient (step 408). In some embodiments, the step 408 may be the same as or similar to step 212 of the method 200 described above.

The method 400 also comprises identifying a predicted location of an anatomical abnormality (step 412). In some embodiments, the anatomical element may be a spinal stenosis. The identifying may be based on the information received in step 404 and the image received in step 408. In some embodiments, the identifying may also be based on the at least one medical record that may be received in step 404. In some embodiments, the identifying may use an identification algorithm such as the identification algorithm 124 to identify the predicted location of the anatomical abnormality. Training data may be used to train the identification algorithm to identify the predicted location of the anatomical abnormality. The training data may include historical data (e.g., data from past patients with the same or similar metrics as the patient; data regarding the same or anatomical abnormalities; data corresponding to historical patient examination results, patient images, patient medical records; etc.).

In some instances, more than one predicted location of more than one anatomical abnormality may be identified (using, for example, the identification algorithm). In such instances, the information provided from the patient examination may be used to identify a specific anatomical abnormality that causes pain and/or discomfort to a patient. In other words, the information corresponding to the patient examination may be used to automatically pinpoint one or more anatomical abnormalities that are most likely to be attributing to pain and/or discomfort of a patient. Thus, unnecessary surgical procedures to correct anatomical abnormalities that less likely to be affecting the patient may be avoided.

The predicted location of the anatomical abnormality may include information about a pose, a position, or an orientation of the anatomical abnormality. For example, in some embodiments, the anatomical abnormality may be an obstruction and the predicted location of the anatomical abnormality may specify a pose, a position, or an orientation of the obstruction.

The method 400 also comprises comparing an anatomical feature at the location of the anatomical abnormality with a corresponding feature at a different location (step 416). The comparison may aid in identifying or confirming the location of the anatomical abnormality. For example, a first vertebra at a first location or level may be compared to a second vertebra at a second location or level. In the same example, the first vertebra may contain the anatomical abnormality and the second vertebra may not contain the anatomical abnormality. Thus, comparing the first vertebra at the identified location to the second vertebra at the same location may help identify or confirm the location of the anatomical abnormality in the first vertebra.

The method 400 also comprises automatically labelling a portion of the at least one anatomical element to surgically modify (step 420). In some embodiments, the step 408 may be the same as or similar to step 224 of the method 200 described above.

The present disclosure encompasses embodiments of the method 400 that comprise more or fewer steps than those described above, and/or one or more steps that are different than the steps described above.

As noted above, the present disclosure encompasses methods with fewer than all of the steps identified in FIGS. 2, 3, and 4 (and the corresponding description of the methods 200, 300, and 400), as well as methods that include additional steps beyond those identified in FIGS. 2, 3, and 4 (and the corresponding description of the methods 200, 300, and 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, ands modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for planning a surgical procedure comprising:
   receiving, at a processor, information corresponding to an examination of a patient, the examination conducted by a user, wherein the information includes a pathology diagnosis from the user;
   receiving, at the processor, an image of a patient anatomy;
   processing, using the processor, the image of the patient anatomy to identify one or more features in the image and yield a processed image;
   inputting, using the processor, the information and the processed image into an analytical model configured to identify, using artificial intelligence, a pathology location;
   comparing a feature of a first anatomical element at the pathology location with a corresponding feature of a second anatomical element at a different location, wherein the first anatomical element has an anatomical abnormality and the second anatomical element does not have the anatomical abnormality, and wherein the anatomical abnormality is a spinal stenosis;
   automatically grading, using the processor, the spinal stenosis based on the comparison, wherein automatically grading the spinal stenosis includes grading the spinal stenosis on a numerical scale;
   automatically identifying, with the processor and based on the pathology location, the comparison, and the graded spinal stenosis, a surgical modification of the first anatomical element;

automatically labeling, with the processor and based on the surgical modification, at least a portion of the first anatomical element in a three-dimensional model of the patient anatomy; and automatically generating, with the processor and based on the surgical modification, machine readable instructions for at least one surgical step.

2. The method of claim 1, wherein the surgical modification corresponds to removing an identified portion of the first anatomical element.

3. The method of claim 1, wherein the surgical modification corresponds to a decompression procedure.

4. The method of claim 3, wherein the examination of the patient identifies an initial spinal level at which to perform the decompression procedure.

5. The method of claim 1, further comprising:
receiving, at the processor, at least one medical record corresponding to the patient,
wherein the inputting further comprises inputting the at least one medical record into the analytical model.

6. The method of claim 1, wherein the image is obtained from a computer tomography (CT) scan or a magnetic resonance imaging (MRI) scan.

7. The method of claim 1, wherein the image is a first image and the method further comprises:
receiving, by the processor, a second image; and
automatically combining, by the processor, the first image and the second image.

8. The method of claim 7, wherein the first image comprises detailed soft tissue information and the second image comprises detailed bony tissue information.

9. The method of claim 1, wherein the information includes results of one or more of a soft tissue tenderness test, a range of motion test, or a straight leg raise test.

10. The method of claim 1, wherein automatically grading the spinal stenosis includes further grading the spinal stenosis on a color intensity scale.

11. The method of claim 1, wherein identifying the pathology location includes an analysis of how spinal nerves are spread out in the image of the patient anatomy.

12. A method for planning a decompression procedure comprising:
receiving, at a processor from a first database, information corresponding to a patient examination, the information comprising information other than an image, and wherein the information includes text corresponding to a pathology diagnosis from a user;
receiving, at the processor from a second database, an image of a spinal region of a patient;
identifying a location of an anatomical abnormality in the spinal region;
comparing a feature of a first anatomical element at the location of the anatomical abnormality with a corresponding feature of a second anatomical element at a different location, wherein the first anatomical element has the anatomical abnormality and the second anatomical element does not have the anatomical abnormality, and wherein the anatomical abnormality is a spinal stenosis;
identifying, with the processor and using artificial intelligence, a location of the spinal stenosis based on the information and the comparison; and
automatically grading, using the processor, the spinal stenosis based on the comparison, wherein automatically grading the spinal stenosis includes grading the spinal stenosis on a color intensity scale;
automatically identifying, with the processor and based on the location of the anatomical abnormality, the comparison, and the graded spinal stenosis, a surgical modification of the first anatomical element; and
automatically generating, with the processor and based on the surgical modification, machine readable instructions for at least one surgical step.

13. The method of claim 12, further comprising:
automatically labeling, with the processor and in a model of the spinal region of the patient, a portion of at least one vertebra to remove during the decompression procedure targeting the spinal stenosis.

14. The method of claim 13, wherein the at least one surgical step corresponds to removing an identified portion of the at least one vertebra.

15. The method of claim 12, further comprising:
determining a spinal level at which to perform the decompression procedure based on the location of the spinal stenosis.

16. The method of claim 12, further comprising determining whether the spinal stenosis is a lateral stenosis or a central stenosis.

17. The method of claim 12, further comprising:
segmenting, with the processor, the spinal region as depicted in the image to define boundaries of individual elements of the spinal region; and
identifying, with the processor, one or more spinal nerves in the image.

18. A system for performing a decompression procedure comprising:
an interface;
at least one processor; and
a memory storing instructions for execution by the at least one processor that, when executed, cause the at least one processor to:
receive, via the interface, information corresponding to a patient examination, the information comprising information other than an image;
receive a three-dimensional image of at least a portion of an anatomy of a patient;
identify, using artificial intelligence, a predicted location of an anatomical abnormality, wherein the anatomical abnormality is a spinal stenosis;
compare a feature of a first anatomical element at the predicted location of the anatomical abnormality with a corresponding feature of a second anatomical element at a second location, wherein the first anatomical element has the anatomical abnormality and the second anatomical element does not have the anatomical abnormality;
automatically grade, using the processor, the spinal stenosis based on the comparison, wherein automatically grading the spinal stenosis includes grading the spinal stenosis on a numerical scale and a color intensity scale; and
automatically label, in the three-dimensional image and based on the predicted location, the comparison, and the graded spinal stenosis, a portion of the first anatomical element to surgically modify; and
automatically generate, using the processor and based on the portion of the first anatomical element to surgically modify, machine readable instructions for at least one surgical step.

19. The system of claim 18, wherein the memory stores additional instructions for execution by the at least one processor that, when executed, further cause the at least one processor to:

compare the feature of the first anatomical element at the predicted location of the anatomical abnormality with the corresponding feature at a third location.

20. The system of claim 18, wherein the information corresponds to a patient description, provided during the patient examination, of at least one symptom experienced by the patient.

* * * * *